United States Patent
Rubin et al.

(10) Patent No.: US 9,752,110 B2
(45) Date of Patent: *Sep. 5, 2017

(54) METHOD AND COMPOSITIONS OF PRESERVING WINE

(71) Applicant: YSDR, LLC, Las Vegas, NV (US)

(72) Inventors: David Rubin, San Diego, CA (US); Ely Rubin, San Diego, CA (US)

(73) Assignee: YSDR, LLC, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,995

(22) Filed: Oct. 27, 2014

(65) Prior Publication Data
US 2015/0044328 A1    Feb. 12, 2015

Related U.S. Application Data

(63) Continuation-in-part of application No. 12/986,952, filed on Jan. 7, 2011, now Pat. No. 8,871,284, which is a continuation-in-part of application No. 12/350,332, filed on Jan. 8, 2009, now abandoned.

(60) Provisional application No. 61/019,745, filed on Jan. 8, 2008.

(51) Int. Cl.
| C12G 1/02 | (2006.01) |
| A61K 31/047 | (2006.01) |
| A61K 31/09 | (2006.01) |

(52) U.S. Cl.
CPC .............. *C12G 1/02* (2013.01); *A61K 31/047* (2013.01); *A61K 31/09* (2013.01); *C12G 2200/21* (2013.01)

(58) Field of Classification Search
CPC ......... A23L 1/00; C12G 1/02; C12G 2200/21; A61K 31/09; A61K 31/047; C12H 1/14
USPC .......................................... 426/15, 542, 590
See application file for complete search history.

(56) References Cited

U.S. PATENT DOCUMENTS

2011/0104328 A1    5/2011    Rubin et al.

FOREIGN PATENT DOCUMENTS

| AU | 2007-101055 A4 | 12/2007 |
| CN | 2005-1699539 A | 11/2005 |
| EP | 1140050 B1 | 12/2003 |
| JP | 2006-52217 A | 2/2006 |
| KR | 10-2006-132059 A | 12/2006 |
| WO | WO-97/39632 A1 | 10/1997 |
| WO | WO-00/38620 A2 | 7/2000 |
| WO | WO 01/08671 A2 | 2/2001 |
| WO | WO-2005/80543 | 9/2005 |
| WO | WO 2005/082407 A1 | 9/2005 |
| WO | WO-2007/094827 A2 | 8/2007 |
| WO | WO-2007/112366 A2 | 10/2007 |
| WO | WO-2007/146318 A2 | 12/2007 |
| WO | WO 2009/089334 A1 | 7/2009 |

OTHER PUBLICATIONS

Amorati et al., "Antioxidant activity of hydroxystilbene derivatives in homogeneous solution," *J. Org. Chem.*, 2004, 69:7101-7107.
Chan, "Antimicrobial effect of resveratrol on dermatophytes and bacterial pathogens of the skin," *Biochem. Pharmacol.*, Jan. 15, 2002, 63(2):99-104.
Danilewicz, "Interaction of sulfur dioxide, polyphenols, and oxygen in a wine-model system: Central role of iron and copper," *Am. J Enol. Vitic.*, 2007, 58:53-60.
Docherty, "Resveratrol selectively inhibits *Neisseria gonorrhoeae* and *Neisseria meningitidis*," *J. Antimicrobial Chemotherapy*, 2001, 47:239-246.
Farina et al., "An improved synthesis of resveratrol," *Nat. Prod. Res.*, Mar. 2006, 20(3):247-252.
Iuga et al., "Antioxidant activity of trans-resveratrol toward hydroxyl and hydroperoxyl radicals: A quantum chemical and computational kinetics study," *J. Org. Chem.*, 2012, 77:3868-3877.
Kukrić et al., "Antibacterial activity of cis- and trans-resveratrol isolated from *Polygonum cupidatum* rhizome," APTEFF, 2006, 37:131-136.
Ribereau-Gayon et al., *Handbook of Enology*, vol. 1, 2000, John Wiley & Sons, pp. 179-180.
Ribereau-Gayon et al., *Handbook of Enology*, vol. 1, 2000, John Wiley & Sons, pp. 35, 379-380.
Rimando et al., "Cancer chemopreventive and antioxidant activities of pterostilbene, a naturally occuring analogue of resveratrol," *J. Agric. Food Chem.*, 2002, 50:3453-3457.
Shang et al., "Radical-scavenging activity and mechanism of resveratrol-oriented analogues: Influence of the solvent, radical, and substitution," *J. Org. Chem.*, 2009, 74:5025-5031.
Wallerath et al., "A blend of polyphenolic compounds explains the stimulatory effect of red wine on human endothelial NO synthase," *Nitric Oxide*, Mar. 2005, 12(2):97-104.
Wikipedia The Free Encyclopedia, "Resveratrol," http://en.wikipedia.org/wiki/resveratrol, accessed Jan. 4, 2008, 15 pages.
Wikipedia The Free Encyclopedia, "Pterostilbene," http://en.wikipedia.org/wiki/pterostilbene, accessed Oct. 28, 2007, 3 pages.
Examination Report dated Apr. 30, 2013, from corresponding Australian Patent Application No. 2009204177, 3 pages.
Examination Report dated Jan. 5, 2014, from corresponding Canadian Patent Application No. 2,711,734, 4 pages.
Examination Report dated Jan. 15, 2015, from corresponding Canadian Patent Application No. 2,711,721, 3 pages.
International Search Report and Written Opinion dated May 29, 2009, from International Patent Application No. PCT/US2009/030421, 7 pages.
International Search Report in International Application No. PCT/US2015/057663, dated Jan. 14, 2016, in 2 pages.

(Continued)

*Primary Examiner* — Vera Stulii
(74) *Attorney, Agent, or Firm* — Duane Morris LLP

(57) ABSTRACT

Resveratrol and/or pterostilbene are added to wines to preserve the wine from oxidation, bacteria and fungi, as well as to deliver resveratrol to an animal. The resveratrol and/or pterostilbene are also added to red wine to preserve the polyphenols present in red wine. The resveratrol and/or pterostilbene can be added to grape must prior to fermentation and/or to fermented wine prior to bottling.

14 Claims, No Drawings

(56) References Cited

OTHER PUBLICATIONS

Louvaud-Funel et al., "Lactic Acid Bacteria in the Quality Improvement and Depreciation of Wine," (Article in Antonie Van Leeuwenhoek) (Published Jan. 1999) Retrieved from the internet on Dec. 22, 2015, URL: https://www.researchgate.net/profile/Aline_Lonvaud-Funel/publication/12769012_Lactic_acid_bacteria_in_the_quality_improvement_and_depreciation_of_wine/links/0fcfd509516c0cd717000000.pdf.

Patent Examination Report No. 1 in Australian Patent Application No. 2015201229, dated Jan. 29, 2016, in 3 pages.

METHOD AND COMPOSITIONS OF PRESERVING WINE

RELATED APPLICATIONS

This application is a Continuation-In-Part Application of U.S. patent application Ser. No. 12/986,952, filed on Jan. 7, 2011, now U.S. Pat. No. 8,871,284, which is a Continuation-In-Part of U.S. patent application Ser. No. 12/350,332, filed on Jan. 8, 2009, now abandoned, which claims priority to United States Provisional Application No. 61/019,745, which was filed on Jan. 8, 2008, the contents of which are each incorporated herein by reference in their entireties.

FIELD OF THE INVENTION

The present application relates to a method and compositions for preserving wine and as well as preserving the antioxidant polyphenols that are present in red wine.

BACKGROUND

Wine is traditionally defined as an alcoholic beverage produced when fruit undergoes primary fermentation in which yeast converts the sugar in fruit to alcohol. When the sugar supply is exhausted, the yeast dies off, leaving the alcohol produced to blend with, or attach to, other components.

Almost all wine improves with aging. However, peak flavor and bouquet may require years to develop in wines with high concentrations of tannins, and many wines deteriorate not long after reaching their peak. Chemical reactions during the aging process are extremely complex and well documented. The desirable characteristics of wine result from a blending of the components in the wine.

Wines without high concentrations of tannins develop flavor and bouquet more rapidly. These wines may also deteriorate not long after reaching their peak.

The traditional wine aging process is simple, well known, and well understood. Oxidation is among the greatest problems with which a winemaker deals during the making and aging process for wine. Oxidation can adversely affect the fruity flavor and freshness of wine. In order to prevent oxidation of the wine, sulfur dioxide (as potassium metabisulfite or sodium metabisulfite) is frequently added to grape must before fermentation to inhibit or kill all unwanted bacteria prior to the point at which the alcohol production commences after fermentation begins. The metabisulfite salts are converted to sulfur dioxide, which is the so-called "free sulfite" of wine. After fermentation produces some alcohol, the sterilizing effects of alcohol assist in killing the unwanted bacteria.

In some wines, particularly those of the Sauternes type, a considerable quantity of naturally-occurring sulfur dioxide is retained in the wine until the wine is bottled. In red wines and in some white wines, sulfur dioxide is added to prevent the wine from becoming unsound.

When sulfur dioxide is first added in the free state, it rapidly combines with other substances in the wine, so that sometimes in a few minutes, and, in other cases, in as much as thirty minutes, the amount of free sulfur dioxide is halved. Over a period of weeks or months, the exact rate of disappearance depends upon many factors, such as temperature and amount of aeration, whereby the total sulfur dioxide content of the wine falls.

During the normal aging process for wine, the conditioners and preservatives, such as sulfur dioxide, are dispersed throughout the liquid. Changes in the wine following bottling are subtle and difficult to establish, since there are no measurements other than taste and smell that are used to determine when the aging process is complete and when the wine invariably begins its decline. Further, the ingredients used vary among wines and winemakers, and each ingredient may affect the aging process differently.

There is a direct relation between the amount of sulfite added and the inhibition of bacterial growth in wine. As such, large scale wine producers, whose risks are high, may use a relatively high concentration of additives such as sulfite to avoid spoilage. However, with the addition of large amounts of sulfites, the wine can be adversely affected, irrespective of the lack of bacterial deterioration.

Some smaller wine producers advertise that they do not use sulfite. This is important to many consumers, as some consumers complain of headaches which are attributed to the presence of sulfite in wines, even though all wines contain a small amount of naturally occurring sulfites. Although the relationship between sulfites in wine and headaches has not been clinically confirmed, many believe that the link is real. As such, wines not containing added sulfites may command a higher retail price, because manufacturing costs are higher and the risk of losing entire batches of wine to bacterial contamination and/or oxidation is borne by the consumer.

Although all wines naturally contain some sulfites as a result of the fermentation process, the amounts of these sulfites are not noticeable to most people. However, when sulfites are added to the must, during fermentation and more so after bottling, gaseous hydrogen sulfide develops in the wine. This gas is extremely toxic and, in many cases, may destroy what would otherwise be a good wine. The concept of decanting the wine, or letting the wine "breathe", in essence allows the hydrogen sulfide to volatilize out of the wine so that it is then suitable for drinking There is no nutritional value to the sulfites added to wine, and, in the case of sodium metabisulfite, consumers may wish to avoid additional sodium as well.

Red wine contains a number of antioxidant polyphenols, which scavenge free radicals and up-regulate certain metal chelation reactions. The polyphenols can reduce inflammatory effects such as coronary artery disease and can inhibit the growth or occurrence of mammalian tumors.

Consuming dietary polyophenols may be associated with beneficial effects in higher animal species, including reduction in inflammatory effects such as coronary artery disease, including improved endothelial health via down-regulation of oxidative LDL and anti-aging consequences such as slowing the process of skin wrinkling.

A high intake of polyphenols is likely to have beneficial effects on the cardiovascular system. Red wine is a rich source of polyphenols, and it has been demonstrated that trans-resveratrol, 3,4',5-trihydroxy-trans-stilbene, has been found to be the most efficacious stimulator of eNOS expression, which enzyme is protective of the cardiovascular system. However, the presence of resveratrol alone could not explain the total stimulatory effect of red wine. The flavanols catechin and epicatechin, the flavanols fisetin, myricetin, isoquercetin and hyperoside, the anthocyanins delphinidin, malvidin and paeodnidin, gallic acid, and the hydroxycinnamic acids ferulic acid and sinapinic acid did not change eNOS expression or eNOS promoter activity in any substantial way. The anthocyanin cyanidin, the hydroxycinnamic acids p-coumaric acid and caffeic acid, and the phenolic acids benzoic acid and vanillic acid also enhanced eNOS expression moderately. Thus, the increase in eNOS in response to ingestion of red wine involves several polyphenolic compounds, with trans-resveratrol making a major contribution, and lesser contributions from cinnamic and hydrocinnamic acids, cyaniding and some phenolic acids. [*Nitric Oxide*, 2005, 12 (2): 97-104]

Sulfur dioxide has been shown to interact with polyphenols and oxygen in wine, which reaction is catalyzed by the presence of copper and iron, which are naturally found in wine grapes Danielewicz, *Am. J. Enol. Vitic.* 58(1): 53-60 2007.

SUMMARY OF THE INVENTION

It has now been discovered that resveratrol; pterostilbene, a natural methoxylated analogue of resveratrol; or a combination of the two compounds, can be used as an antioxidant, fungicide and bactericide in wine. Resveratrol and pterostilbene have no known side effects in humans, and can be used as a replacement for sulfites that are conventionally added to wines as preservatives.

In addition, the resveratrol, pterostilbene or a combination thereof are also used to preserve the antioxidant polyphenols in red wine.

The resveratrol, pterostilbene, or combination thereof, can be added to the grape must prior to fermentation, during fermentation, and at the time of bottling the wine. Since the yeast during fermentation and the alcohol produced during fermentation do not adversely affect the pterostilbene or resveratrol, the time of addition of these compounds is not critical.

Grapes, and some other fruits and vegetables such as Vaccinium berries, normally produce resveratrol as a defense mechanism when being attacked by some extraneous fungi, bacteria or insects. However, the amount of resveratrol the fruit or vegetable produces is only sufficient to protect the individual fruit or vegetable, but it is not nearly enough to protect an entire batch of wine produced from grapes (about 5 mg/kg in red wine). Moreover, different grape varieties produce different amounts of resveratrol.

Resveratrol and/or pterostilbene, whether naturally occurring or synthetic, can be added to wine to act as a preservative. These compounds can be added to wine in amounts ranging from about 5 mg/L to about 11,500 mg/L, ideally, the compounds should be added twice. It is preferable to add pterostilbene during the first step of fermentation because it is less water soluble than resveratrol and thus will create a thin film layer on top of the must, further preventing contact with oxygen and preventing decomposition of the pterostilbene. Resveratrol, which is more stable than pterostilbene, can then be added to finished wine to act as an antioxidant during aging and storage of the wine.

Resveratrol and pterostilbene also have antibacterial and antifungal activity in wine. (Biochem. Pharmacol. January 2002 15; 63(2) 99-104).

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

DETAILED DESCRIPTION

Resveratrol, 3,4'-dihydroxystilbene, also known as 3,4', 5-stilbenetriol, is a phytoalexin produced naturally by several plants when under attack by bacteria or fungi. Resveratrol has also been produced synthetically (see Farina et al., *Nat. Prod. Res.* 20(3): 247-252, 2006).

Pterostilbene is a stilbenoid compound that is an analogue of resveratrol. Other names for pterostilbene are 4-[(E)-2, (3,5-dimethoxyphenyl)ethenyl]phenol; 3',4'-dimethoxy-4-stilbenol; and 3,5-dimethoxy-4'-hydroxy-trans-stilbene.

In grapes, resveratrol is found in the skin and seeds. The amount found in grape skins varies with the grape cultivar, its geographic origin, and exposure to fungal infection. The amount of time wine spends in contact with grape skins is an important determinant of its resveratrol content.

Table 1 illustrates resveratrol content in several types of wines

TABLE 1

| Beverage | Total Resveratrol, mg/L |
| --- | --- |
| Muscadine wine | 14.1-40 |
| Red wines (Global) | 1.98-7.13 |
| Red wines (Spanish) | 1.92-12.59 |
| Red grape juice (Spanish) | 1.1-8.69 |
| Rose wines (Spanish) | 0.43-3.52 |
| Pinot noir | 0.40-2.0 |
| White wine (Spanish) | 0.05-0.80 |

As can be seen from Table 1, ordinary non-muscadine red wine contains between 0.4 and 12.59 mg/L of resveratrol, depending upon the grape variety. White wine contains much less resveratrol. This is because red wine is fermented with the skins, allowing the wine to absorb the resveratrol, whereas white wine is fermented after the skins have been removed from the grapes. Additionally, red grape skins have more resveratrol than white grape skins. However, wine grapes that have been sprayed with pesticides that prevent fungal infection contain little, if any, resveratrol, because there is no need for the grapes to protect themselves from fungal infection by producing resveratrol. Wine grapes grown in dry climates have less resveratrol than those grown in humid areas.

It can readily be seen that the amount of resveratrol in wines is extremely low, so that additional resveratrol or pterostilbene must be added to wines to preserve the wine from oxidation, bacteria and fungi. This is true for red wines, rose wines, and white wines.

Quantitative studies of resveratrol in plants have found that there are only one to two parts pterostilbene per ten parts of resveratrol. The relationship between the two compounds and their unequal content in plants is unclear, but it remains the subject of ongoing studies. Dark-skinned grapes are likely to contain the most pterostilbene. For reasons that are not clear, pterostilbene is normally not found in wine. This may be because it is unstable in light and air, which makes it less likely to survive the wine making process.

The following examples are for purposes of illustrating the invention, and are not meant to be limiting in any way.

EXAMPLE 1

Cabernet Sauvignon and Shiraz were each aged in French barrels (225 liter). One barrel of the Cabernet Sauvignon was preserved with resveratrol, and one was preserved with sodium metabisulfite. One barrel of Shiraz was preserved with resveratrol, and the other barrel of Shiraz was preserved with sodium metabisulfite. All of the barrels were aged for twelve months.

The Cabernet and Shiraz treated with resveratrol had a much more intense color than the Cabernet and Shiraz preserved with sodium metabisulfite.

The wines preserved with resveratrol had a fresh and fruity taste. The wines preserved with metabisulfite had a slight sulfur smell which was eliminated by allowing the wine to breathe for a few minutes prior to drinking.

EXAMPLE 2

One gram (1000 mg) of resveratrol was dissolved in one liter of 12.5% alcohol non-sulfated Cabernet Sauvignon. While the variety of wine would not make much difference, the alcohol content of the wine might have some effect on spoilage, as a wine having a higher concentration of alcohol would need less resveratrol to control spoilage.

The resveratrol enriched wine was stored in an open bottle at room temperature. The wine retained its taste and color for more than five months, despite the exposure to atmospheric oxygen and ambient bacteria and fungi. This is in contrast to similar wines to which sulfite has been added which, once exposed to oxygen, began to deteriorate within a few hours.

EXAMPLE 3

All the different studies indicated that resveratrol can successfully replace SO2 in the preservation of wine, and that resveratrol is a superior preservative for wine.

The following parameters were compared: ph, density, Brix and browning (indication of oxidation) in different waves lengths: 280 nm, 420 nm 520 nm and 62 nm.

The pH is a measure of the acidity of wine. If wine is too low in acid, it tastes flat and dull. If a wine is too high in acid, it tastes too tart and sour. If the pH of a wine is above about 4.0, the wine becomes unstable with respect to microorganisms; a low pH inhibits growth of microorganisms.

The principal acids found in grapes, and therefore in wine, are tartaric acid, potassium hydrogen tartrate (cream of tartar), malic acid and potassium hydrogen malate. Tartaric acid and malic acid are produced by the grapes as they develop. The warmer the climate in which the grapes grow, the higher is the sugar content and the lower is the acidity. Conversely, grapes grown in a cooler climate have a lower sugar content and a higher acidity. A winemaker can manipulate the acidity and sugar levels to produce a wine having the desired characteristics.

Malolactic fermentation is a natural process by which acidity is adjusted. This process lowers the acidity by converting malic acid to lactic acid and carbon dioxide. Nearly all red wines undergo malolactic fermentation.

Brix is a measure of the sugar content of the grape juice at harvest. At normal fruit maturity, growth ceases and accumulation of sugar cease at about 25 Brix. Further increases in sugar content result from water loss as the grape develops into a raisin, which is only desirable in late harvest wines. The desirable range for table wines is between 19.5 and 23.5 in free-run grape juice prior to fermentation.

Density, or specific gravity, of a wine increases as the amount of sugar in the wine increases. The density falls during fermentation as the yeasts convert the sugar to alcohol. Finished wine should have a density of between about 1.010 and 0.990, for sweet and dry wine, respectively.

Oxidative browning in wine has traditionally been controlled by addition of sulfur dioxide to the wine. Browning is due to oxidation of the polyphenolic compounds present in wines. In organoleptic terms, this phenomenon translates into a process of continuous oxidation, a loss of aromatic freshness, and, in the final stages, in the appearance of precipitates of condensed phenolic material in the bottled wine.

Extensive testing was conducted by The Israel Wine Institute on red wines to determine the preservative effects of resveratrol on red wines, particularly in persevering the polyphenols contained in these wines. Two red grapes, cabernet sauvignon and shiraz were used.

The study ran 12 batches for each kind of wine: 3 controls, with no additives; 3 with 100 ppm $SO_2$, the accepted industry standard; 3 with low dose resveratrol, 300 ppm; and 3 with high dose resveratrol, 3000 ppm. The resveratrol was added in about 1:1 stoichiometric ratio and 10 times the stoichiometric ratio of the sulfite used.

Fermentation was in 225 L barrels. After 12 months of fermentation the wines were tested as described above.

The color of the cabernet sauvignon and shiraz preserved with resveratrol was much more intense for the wines preserved with resveratrol than for the control wines or the wines preserved with sodium metabisulfite.

The wines preserved with resveratrol had a fresh and fruity fragrance, as opposed to a slight sulfuric odor and taste in the wines preserved with sodium metabisulfite. It is the slight amount of $SO_2$ present in wines preserved with metabisulfite that makes it desirable to decant the wines prior to serving.

The results of the analytical studies tabulated above show the differences in colors among the wines treated with metabisulfite and resveratrol.

In addition to the difference in the wavelength of the absorption of anthocyanadins and other pigments of the differently preserved wines, it was also discovered from the absorption spectra that the metabisulfite metabolites, primarily $SO_2$, reacted with the polyphenols to form sulfate conjugates by attacking the hydroxyl groups of the polyphenols, which renders the anthocyanadins and the proanthocyanadins substantially less active antioxidants.

Clearly, the wine preserved with resveratrol is considerably richer in nonconjugated antioxidants than wine preserved with metabisulfite. For this reason, wines preserved with resveratrol are probably more nutritionally valuable than wines preserved with metabisulfite. It should also be noted that resveratrol is a strong antioxidant in its own right, as well as a known precursor to the important telomerase enzyme.

The amount of pterostilbene added to wine should be about 15% more than the amount of resveratrol.

Treatment No. 1 was a control, with no addition of any type of preservative.

Treatment No. 2 was a two-stage treatment with metabisulfite, the current standard for preserving wines. Stage 1, the metabisulfite was added prior to fermentation at a rate of 50 mg/L. After malic and lactic fermentation 75 mg/L of metabisulfite was added.

Treatment No. 3 was addition of resveratrol. Before fermentation; 180 mg/L resveratrol was added prior to putting the wine into barrels for fermentation. After fermentation, 176 g/L resveratrol was added.

Each treatment was repeated five times. The results are shown in Tables 2-7.

Tables 8-10 show the results when about 15% "Petit Verdu" was added to improve the color of wine made from cabernet sauvignon grapes. This is a conventional blend, with the cabernet sauvignon grapes predominating in the wine.

TABLE 2

Details of Treatment of Variety Cabernet Sauvignon

| weight of grapes (kg) | Wine No. | Repetition | Grape Variety | Treat |
|---|---|---|---|---|
| 30 | 1 | I | Cabernet Sauvignon | Control (no additive) |
| 30 | 2 | II | | |
| 30 | 3 | III | | |
| 30 | 4 | IV | | |
| 30 | 5 | V | | |
| 90 | 6 | I | | Addition of SO$_2$ |
| 90 | 7 | II | | |
| 90 | 8 | III | | |
| 90 | 9 | IV | | |
| 90 | 10 | V | | |
| 90 | 11 | I | | Addition of Resveratrol |
| 90 | 12 | II | | |
| 90 | 13 | III | | |
| 90 | 14 | IV | | |
| 90 | 15 | V | | |

TABLE 3

Details of Treatment of Variety Shiraz

| weight of grapes (kg) | Wine No. | Repetition | Grape Variety | Treat |
|---|---|---|---|---|
| 30 | 1 | I | Shiraz | Control (no additive) |
| 30 | 2 | II | | |
| 30 | 3 | III | | |
| 30 | 4 | IV | | |
| 30 | 5 | V | | |
| 90 | 6 | I | | Addition of SO$_2$ |
| 90 | 7 | II | | |
| 90 | 8 | III | | |
| 90 | 9 | IV | | |
| 90 | 10 | V | | |
| 90 | 11 | I | | Addition of Resveratrol |
| 90 | 12 | II | | |
| 90 | 13 | III | | |
| 90 | 14 | IV | | |
| 90 | 15 | V | | |

TABLE 4

Brix Test, Total Acidity (T.A.) pH of Potassium in "new wine" (Thawed Juice)

| K (mg/l) | pH | T.A. (g/l) | (%) Brix | Treat | Serial No. |
|---|---|---|---|---|---|
| 1790 | 4.00 | 3.1 | 22.8 | Control | 1 |
| 1760 | 4.09 | 3.1 | 21.2 | | 2 |
| 1930 | 4.12 | 3.1 | 21.8 | | 3 |
| 1820 | 4.08 | 2.9 | 21.5 | | 4 |
| 2050 | 4.15 | 3.2 | 22.5 | | 5 |
| 1790 | 4.00 | 3.1 | 22.8 | Addition of SO$_2$ | 6 |
| 1760 | 4.09 | 3.1 | 21.2 | | 7 |
| 1930 | 4.12 | 3.1 | 21.8 | | 8 |
| 1820 | 4.08 | 2.9 | 21.5 | | 9 |
| 2050 | 4.15 | 3.2 | 22.5 | | 10 |
| 1790 | 4.00 | 3.1 | 22.8 | Addition of Resveratrol | 11 |
| 1760 | 4.09 | 3.1 | 21.2 | | 12 |
| 1930 | 4.12 | 3.1 | 21.8 | | 13 |
| 1820 | 4.08 | 2.9 | 21.5 | | 14 |
| 2050 | 4.15 | 3.2 | 22.5 | | 15 |

We believe that the low acidity value obtained was a result of the testing on thawed "new wine due to seasons. The HPLC Analysis showed volumes of 4 g of tartaric acid.

TABLE 5

Analysis during fermentation process were done to test the in sugar during fermentation as detailed below

| 12.10.09 After decanting | 11.10.09 After pressing | 07.10.09 | 06.10.09 | 3 days after fermentation | | | Treat | Serial No. |
|---|---|---|---|---|---|---|---|---|
| 995.2 | 994.8 | | | | | | Control | 1 |
| 995.1 | 995.2 | | | | | | | 2 |
| 995.2 | 995.3 | | | 1020.4 | 1040 | 3.84 | | 3 |
| 995.1 | 994.8 | | | | | | | 4 |
| 994.7 | 994.9 | | | | | | | 5 |
| 994.6 | 995.2 | 1000.4 | 1006.9 | | | | Addition of SO$_2$ | 6 |
| 995.2 | 995.3 | 997.4 | 1004.4 | | | | | 7 |
| 995.2 | 995.2 | | | 1015.1 | 1034 | 3.78 | | 8 |
| 995.1 | 995.3 | | | | | | | 9 |
| 994.6 | 995.2 | | | | | | | 10 |
| 995.2 | | | | | | | Addition of Resveratrol | 11 |
| 995.6 | | | | | | | | 12 |
| 995.2 | | 997.4 | 1002.9 | 1016.7 | 1037 | 3.81 | | 13 |
| 994.6 | | 998.4 | 1005.4 | | | | | 14 |
| 994.6 | | 998.4 | 1005.4 | | | | | 15 |

TABLE 6

Tests of progressing of Malic and Lactic Fermentation Qualitative Thin Layer Chromatography (TLC) showed completion of fermentation. Qualitative results were confirmed by quantitative HPLC. Results of Qualitative Analysis of Malic and Lactic acid in Cabernet Sauvignon

| Lactic Acid | Malic Acid | Treat |
|---|---|---|
| 1.57 | 0.05 | Control |
| 1.41 | 0.03 | Addition of $SO_2$ |
| 1.47 | 0.05 | Addition of Resveratrol |

TABLE 7

Data of Color of Particles (?) of Cabernet Sauvignon

| Malvidin-3-glucoside Amount (mg/l) | Color Intensity 520 | 420 | Average particle weight (g) | Sample wine | Serial No. |
|---|---|---|---|---|---|
| 37.4 | 0.129 | 0.042 | 1.22 | Control | 1 |
| 67.1 | 0.175 | 0.060 | 1.15 | | 2 |
| 59.4 | 0.163 | 0.054 | 1.19 | | 3 |
| 65.8 | 0.173 | 0.056 | 1.18 | | 4 |
| 60.6 | 0.165 | 0.056 | 1.22 | | 5 |
| 37.4 | 0.129 | 0.042 | 1.22 | Addition of $SO_2$ | 6 |
| 67.1 | 0.175 | 0.060 | 1.15 | | 7 |
| 59.4 | 0.163 | 0.054 | 1.19 | | 8 |
| 65.8 | 0.173 | 0.056 | 1.18 | | 9 |
| 60.6 | 0.165 | 0.056 | 1.22 | | 10 |
| 37.4 | 0.129 | 0.042 | 1.22 | Addition of Resveratrol | 11 |
| 67.1 | 0.175 | 0.060 | 1.15 | | 12 |
| 59.4 | 0.163 | 0.054 | 1.19 | | 13 |
| 65.8 | 0.173 | 0.056 | 1.18 | | 14 |
| 60.6 | 0.165 | 0.056 | 1.22 | | 15 |

"Petit Verdu" was added to improve color of Cabernet wine "Petit Verdu"

TABLE 8

Brix Test, pH, K, total acidity (T.A.) for "new wine", Petit Verdu

| K (mg/l) | pH | T.A. (g/l) | Brix (%) | Treat | Serial No. |
|---|---|---|---|---|---|
| 2700 | 3.86 | 4.63 | 24.3 | Petit Verdu | 1 |
| 2690 | 3.94 | 4.73 | 24.7 | | 2 |

Analysis of Wines

TABLE 9

Results of Testing Cabernet Blend and Alcoholic Fermentation (22.11.09)

| Total Phenols (mg/l) | Reducing Sugars (g/l) | V.A. (g/l) | T.A. (g/l) | pH | Specific Gravity | Alcohol (%) | $SO_2F$ (mg/l) | $SO_2T$ (mg/l) | Treat |
|---|---|---|---|---|---|---|---|---|---|
| 1615 | 1.46 | 0.60 | 6.32 | 3.67 | 995.0 | 12.8 | 26.0 | 75 | $SO_2$ |
| 1938 | 1.27 | 0.60 | 5.95 | 3.73 | 994.5 | 12.6 | 0.0 | 10 | Resveratrol |

Color Analysis

TABLE 10

Color Analysis of Cabernet Blend Wines (22.11.09)

| 620 | 520 | 420 | Treat |
|---|---|---|---|
| 0.032 | 0.207 | 0.159 | $SO_2$ |
| 0.076 | 0.315 | 0.217 | Resveratrol |

Brix Test, pH, K, Total Acidity (T.A.) for "New Wine"

TABLE 11

Brix Test, pH, K, total acidity (T.A.) for "new wine", Shiraz (08.09.09)

| K | PH | T.A. (g/l) | (%) Prix | Treat | Serial No. |
|---|---|---|---|---|---|
| 2120 | 3.89 | 3.77 | 23.6 | Control | 1 |
| 2100 | 3.81 | 3.92 | 23.3 | | 2 |
| 2220 | 3.79 | 4.65 | 23.5 | | 3 |
| 2240 | 3.79 | 4.61 | 23.9 | | 4 |
| 2050 | 3.79 | 4.85 | 23.7 | | 5 |
| 2120 | 3.89 | 3.77 | 23.6 | Addition of $SO_2$ | 6 |
| 2100 | 3.81 | 3.92 | 23.3 | | 7 |
| 2220 | 3.79 | 4.65 | 23.5 | | 8 |
| 2240 | 3.79 | 4.61 | 23.9 | | 9 |
| 2050 | 3.79 | 4.85 | 23.7 | | 10 |
| 2120 | 3.89 | 3.77 | 23.6 | Addition of Resveratrol | 11 |
| 2100 | 3.81 | 3.92 | 23.3 | | 12 |
| 2220 | 3.79 | 4.65 | 23.5 | | 13 |
| 2240 | 3.79 | 4.61 | 23.9 | | 14 |
| 2050 | 3.79 | 4.85 | 23.7 | | 15 |

Analysis of Fermentation Process

TABLE 12

Analysis Tests of Regular Intervals of Density to Test Sugar During Fermentation as Shown Below

| Density after 1st decanting | Density (???) after pressing | pH | Treat | Serial No. |
|---|---|---|---|---|
| 0.9927 | 0.9941 | 3.81 | Control | 1 |
| 0.9932 | 0.9946 | 3.82 | | 2 |
| 0.9932 | 0.9944 | 3.91 | | 3 |
| 0.9932 | 0.9952 | 3.86 | | 4 |
| 0.9932 | 0.9951 | 3.98 | | 5 |
| 0.9933 | 0.9954 | 3.88 | Addition of $SO_2$ | 6 |
| 0.9933 | 0.9954 | 3.79 | | 7 |
| 0.9933 | 0.9958 | 3.95 | | 8 |
| 0.9938 | 0.9952 | 3.94 | | 9 |
| 0.9938 | 0.9952 | 3.84 | | 10 |

TABLE 12-continued

Analysis Tests of Regular Intervals of Density to Test Sugar During Fermentation as Shown Below

| Density after 1st decanting | Density (???) after pressing | pH | Treat | Serial No. |
|---|---|---|---|---|
| 0.9937 | 0.9946 | 3.91 | Addition of | 11 |
| 0.9937 | 0.9945 | 3.83 | Resveratrol | 12 |
| 0.9932 | 0.9943 | 3.97 | | 13 |
| 0.9933 | 0.9945 | 3.91 | | 14 |
| 0.9932 | 0.9950 | 3.85 | | 15 |

Following Analysis to Test Progress of Fermentation:

Qualitative Thin Layer Chromatography (TLC) that shows completion of fermentation confirmed by quantitative HPLC.

TABLE 13

Results of Qualitative Analysis Thin Layer Chromatography (TLC) for (???) of Malic and Lactic Acids

| 29.09.09 | | 21.09.09 | | | |
|---|---|---|---|---|---|
| Lactic | Malic | Lactic | Malic | Treat | Serial No. |
| + | − | Traces | + | Control | 1 |
| + | − | + | + | | 2 |
| + | − | Traces | + | | 3 |
| + | − | Traces | + | | 4 |
| + | − | Traces | + | | 5 |
| + | − | Traces | + | Addition of | 6 |
| + | − | Traces | + | SO$_2$ | 7 |
| + | − | Traces | + | | 8 |
| + | − | Traces | + | | 9 |
| + | − | Traces | + | | 10 |
| + | − | Traces | + | Addition of | 11 |
| + | − | Traces | + | Resveratrol | 12 |
| + | − | Traces | + | | 13 |
| + | − | Traces | + | | 14 |
| + | − | Traces | + | | 15 |

TABLE 14

Color Data of Shiraz Particles

| Malvidin-3-glucoside Amount (mg/g) | Amount (mg/l) | Color Intensity 520 | 420 | (???) | Sample | Serial No. |
|---|---|---|---|---|---|---|
| 5.2 | 209.7 | 0.396 | 0.105 | 1.10 | Control | 1 |
| 5.9 | 236.8 | 0.438 | 0.115 | 1.10 | | 2 |
| 6.1 | 243.2 | 0.448 | 0.125 | 1.09 | | 3 |
| 6.2 | 247.1 | 0.454 | 0.114 | 1.08 | | 4 |
| 5.1 | 205.2 | 0.389 | 0.106 | 1.09 | | 5 |
| 5.2 | 209.7 | 0.396 | 0.105 | 1.10 | Addition of | 6 |
| 5.9 | 236.8 | 0.438 | 0.115 | 1.10 | SO$_2$ | 7 |
| 6.1 | 243.2 | 0.448 | 0.125 | 1.09 | | 8 |
| 6.2 | 247.1 | 0.454 | 0.114 | 1.08 | | 9 |
| 5.1 | 205.2 | 0.389 | 0.106 | 1.09 | | 10 |
| 5.2 | 209.7 | 0.396 | 0.105 | 1.10 | Addition of | 11 |
| 5.9 | 236.8 | 0.438 | 0.115 | 1.10 | Resveratrol | 12 |
| 6.1 | 243.2 | 0.448 | 0.125 | 1.09 | | 13 |
| 6.2 | 247.1 | 0.454 | 0.114 | 1.08 | | 14 |
| 5.1 | 205.2 | 0.389 | 0.106 | 1.09 | | 15 |

Analysis of Wine

TABLE 15

Results of Analysis of Shiraz Wine Before Adjusting pH

| Total Phenols (mg/l) | Reducing Sugars (g/l) | V.A. (g/l) | T.A. (g/l) | pH | Specific Gravity | Alcohol (%) | SO$_2$F (mg/l) | SO$_2$T (mg/l) | Treat |
|---|---|---|---|---|---|---|---|---|---|
| 1600 | 1.77 | 0.73 | 4.78 | 4.03 | 0.9934 | 14.0 | 16.0 | 64 | SO$_2$ |
| 1961 | 1.81 | 0.79 | 4.68 | 4.04 | 0.9932 | 13.9 | 0.0 | 3 | Resveratrol |

TABLE 16

Color Analysis of Shiraz (22.11.09

| 620 | 520 | 420 | Treat |
|---|---|---|---|
| 0.168 | 0.222 | 0.168 | SO$_2$ |
| 0.237 | 0.401 | 0.237 | Resveratrol |

It is clear from the above that adding resveratrol preserved the anthocyanadins in red wines, which compounds give red wines their distinctive color. These anthocyanadins, as noted above, are preserved because of the greater color intensity of the wines preserved with resveratrol. The same results can be expected from the addition of pterostilbene in about 11.5% of the resveratrol added.

It is clear from the results shown in Tables 2-16 that the resveratrol was more effective than the control or the meta-bisulfite in preserving the colors and thus the polyphenols in red wines.

In addition to preserving the wine, the added resveratrol provides additional benefits to those consuming the wine. Thus, adding resveratrol to wine enhances the nutritional benefits of wine.

Thus, in addition to the findings described above that wine can be preserved with Resveratrol and/or pterostilbene instead of the commonly used sodium meta bi-sulfate, two additional advantages over the conventional (sodium meta bi-sulfate) method were also established. The data obtained from our studies of exemplary red wines, e.g., Shiraz and Cabernet Sauvignon, demonstrated that preservation with resveratrol and/or pterostilbene yielded a higher intensity of the wine color, and also reducing or eliminating the need for an additional step of malolactic fermentation.

In the comparison of wine prepared using resveratrol to control wine prepared using bi-sulfates, (applying the exact same conditions and pH) the intensity of the purple pigment of the resveratrol-made wine was considerably higher than that of the control group. As discussed above, the greater color intensity of the wines preserved with resveratrol indicated that the anthocyanins were also preserved by the resveratrol. Further studies have demonstrated that resveratrol does not react with these molecules. In contrast, sodium meta bi-sulfate causes (to some extent) these molecules to precipitate out to form a sediment. This slow process makes the wine less intense in pigment. Thus, preservation with resveratrol provides a higher level of anthocyanins, which are beneficial anti-oxidants that increase the aging capacity of the wine, and exhibit significant human health benefits.

Another important process in wine-making is the Malolactic fermentation. Malic acid is naturally present in the grape must, but it adds an unpleasant taste to the wine. Wine makers often convert malic acid to lactic acid that possesses a more pleasant taste. As discussed above, nearly all red wines undergo malolactic fermentation. As discussed above, the conversion is usually carried out by introducing a lactobacteria (most commonly the *Oenococus-Oeni lactobacteria*) to the wine after an initial fermentation step. It has also been found that while the sulfates suppress the malolactic conversion, thereby requiring an additional step for the Malolactic Fermentation, the resveratrol is a specific inhibitor of the *acetobacter xilum* and possesses no anti-bacterial properties against any lactobacilus. Therefore, in wine preserved with resveratrol and/or pterostilbene, the malolactic fermentation can take place during the initial alcohol-fermentation process. That is, no separate step of malic and lactic fermentation needs to be carried out when wine is preserved with resveratrol and/or pterostilbene.

The foregoing description of the specific embodiments will so fully reveal the general nature of the invention that others can, by applying current knowledge, readily modify and/or adapt for various applications such specific embodiments without undue experimentation and without departing from the generic concept and, therefore, such adaptations and modifications should and are intended to be comprehended within the meaning and range of equivalents of the disclosed embodiments.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for producing red wine that is free of added sulfite and for preserving the polyphenols in red wine, the method comprising:
   a. contacting grape must with an agent added for bacteriocidal activity, the agent selected from the group consisting of resveratrol, pterostilbene and mixtures thereof;
   b. adding a wine producing yeast to the grape must from step (a);
   c. fermenting the grape must from step (b) to produce wine, the wine containing a quantity of the agent, which quantity is enhanced relative to any natural quantity of the agent in the wine, with the proviso that no sulfites are added at any time during or after production of the wine, and the red wine does not contain any sulfate conjugates of polyphenols formed from added sulfites;
   wherein malolactic fermentation occurs during step (c),
   wherein the red wine that is free of added sulfite comprises from 1 gram/L to about 11.5 grams/L of resveratrol, pterostilbene or mixtures thereof.

2. The method of claim 1, wherein the red wine has greater color intensity than red wine containing added sulfites.

3. The method of claim 1, wherein the red wine has an absorbance at 420λ of greater than 0.2, or an absorbance at 520λ of greater than 0.3.

4. The method of claim 3, wherein the wine is a Cabernet Sauvignon having an absorbance at 520λ of greater than 0.3.

5. The method of claim 3, wherein the wine is a Cabernet Sauvignon having an absorbance at 420λ of greater than 0.2.

6. The method of claim 3, wherein the wine is a Shiraz having an absorbance at 520λ of greater than 0.400.

7. The method of claim 3, wherein the wine is a Shiraz having an absorbance at 420λ of greater than 0.2.

8. The red wine that is free of added sulfite prepared from the method of claim 1, wherein the agent consists essentially of resveratrol.

9. The method of claim 1, wherein the red wine is a Cabernet Sauvignon having an absorbance at 520λ of greater than 0.3.

10. The method of claim 1, wherein the red wine is a Cabernet Sauvignon having an absorbance at 420λ of greater than 0.2.

11. The method of claim 1, wherein the red wine is a Shiraz having an absorbance at 520λ of greater than 0.4.

12. The method of claim 1, wherein the red wine is a Shiraz having an absorbance at 420λ of greater than 0.2.

13. The method of claim 1, wherein the red wine is a Shiraz having an absorbance at 420λ of greater than 0.23.

14. The method of any of claims 3 or 1, wherein the red wine is free of added lactobacteria.

* * * * *